US009186389B2

(12) United States Patent
Kogure et al.

(10) Patent No.: US 9,186,389 B2
(45) Date of Patent: Nov. 17, 2015

(54) NANOPARTICLES CONTAINING PH-RESPONSIVE PEPTIDE

(75) Inventors: Kentaro Kogure, Otsu (JP); Susumu Hama, Otsu (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/113,411

(22) PCT Filed: Apr. 24, 2012

(86) PCT No.: PCT/JP2012/060905
§ 371 (c)(1),
(2), (4) Date: Oct. 23, 2013

(87) PCT Pub. No.: WO2012/147714
PCT Pub. Date: Nov. 1, 2012

(65) Prior Publication Data

US 2014/0044778 A1 Feb. 13, 2014

(30) Foreign Application Priority Data

Apr. 25, 2011 (JP) ................................ 2011-097694

(51) Int. Cl.

| | |
|---|---|
| ***A61K 38/03*** | (2006.01) |
| ***A61K 38/16*** | (2006.01) |
| ***A61K 38/02*** | (2006.01) |
| ***C07K 2/00*** | (2006.01) |
| ***C07K 14/00*** | (2006.01) |
| ***A61K 9/127*** | (2006.01) |
| ***C07K 7/06*** | (2006.01) |
| ***A61K 38/05*** | (2006.01) |
| ***A61K 38/06*** | (2006.01) |
| ***A61K 38/07*** | (2006.01) |
| ***A61K 38/08*** | (2006.01) |
| ***A61K 47/48*** | (2006.01) |

(52) U.S. Cl.
CPC ................ *A61K 38/02* (2013.01); *A61K 9/127* (2013.01); *A61K 38/03* (2013.01); *A61K 38/05* (2013.01); *A61K 38/06* (2013.01); *A61K 38/07* (2013.01); *A61K 38/08* (2013.01); *A61K 38/16* (2013.01); *A61K 47/48815* (2013.01); *A61K 47/48823* (2013.01); *C07K 2/00* (2013.01); *C07K 7/06* (2013.01); *C07K 14/00* (2013.01)

(58) Field of Classification Search
None
See application file for complete search history.

(56) References Cited

U.S. PATENT DOCUMENTS

| | | | | |
|---|---|---|---|---|
| 6,660,843 | B1 * | 12/2003 | Feige et al. | ................ 530/391.7 |
| 2003/0224037 | A1 | 12/2003 | Eriguchi et al. | |

FOREIGN PATENT DOCUMENTS

| | | | | |
|---|---|---|---|---|
| JP | 2004010481 A | 1/2004 | | |
| JP | 2004523531 A | 8/2004 | | |
| JP | 2008214324 A | 9/2008 | | |
| WO | 02059147 A2 | 8/2002 | | |
| WO | WO02/059147 * | 8/2002 | ............. | A61K 38/17 |
| WO | 2006/057633 A2 | 6/2006 | | |
| WO | 2007/096899 A2 | 8/2007 | | |
| WO | WO2009/106073 * | 9/2009 | ............. | A61K 39/02 |

OTHER PUBLICATIONS

CAS Registry: Exact and pattern searching of protein sequences, CAS, 2008.*
Asanuma et al., Structural evidence of α-aminoacylated lipoproteins of *Staphylococcus aureus*, FEBS Jl., (2011) 716-728.*
Ganta et al., A review of stimuli-responsive nanocarriers for drug and gene delivery, Journal of Controlled Release, vol. 126, No. 3, 2008, pp. 187-204.
Wei Yu et al., Enhanced transfection efficiency of a systemically delivered tumor-targeting immunolipoplex by inclusion of a pH-sensitive histidylated oligolysine peptide, Nucleic Acids Research, vol. 32, No. 5, 2004, pp. 1-10.
Extended European Search Report dated Nov. 28, 2014 for the corresponding EP Patent Application No. 12777710.0, 5 pgs.
Guo et al., "Core/Shell pH-Sensitive Micelles Self-Assembled from Cholesterol Conjugated Oligopeptides for Anticancer Drug Delivery", American Institute of Chemical Engineers Journal, 2010, vol. 56, No. 7, pp. 1922-1931.
Oh et al., "pH-sensitive properties of surface charge-switched multifunctional polymeric micelle", International Journal of Pharmaceuctics, 2009, vol. 376, pp. 134-140.

* cited by examiner

*Primary Examiner* — Karlheinz R Skowronek
*Assistant Examiner* — Joseph Fischer
(74) *Attorney, Agent, or Firm* — Rothwell, Figg, Ernst & Manbeck, P.C.

(57) ABSTRACT

The present invention provides a nanoparticle and cell delivery agent, capable of releasing a target substance in a weakly acidic pH environment. Specifically, the present invention provides a nanoparticle comprising a peptide and a particle-forming component, the particle-forming component forming a liposome or a micelle, the peptide having a sequence with 2 to 8 units starting with His (histidine) and ending with an acidic amino acid, wherein each of the units may be identical or different.

3 Claims, 7 Drawing Sheets

| | Component name | Retention time (min) | Area (μV·sec) | %Area | Height (μV) | Concentration | Unit |
|---|---|---|---|---|---|---|---|
| 1 | | 10.308 | 32875 | 0.41 | [illegible] | | |
| 2 | | 15.100 | 7976844 | 99.59 | 710487 | | |

|  | Component name | Retention time (min) | Area (μV sec) | %Area | Height (μV) | Concentration | Unit |
|---|---|---|---|---|---|---|---|
| 1 |  | 8.200 | 42341 | 0.56 | 8980 |  |  |
| 2 |  | 8.374 | 7458078 | 98.38 | 931044 |  |  |
| 3 |  | 13.280 | 80620 | 1.07 | 4550 |  |  |

NANOPARTICLES CONTAINING PH-RESPONSIVE PEPTIDE

TECHNICAL FIELD

The present invention relates to a weakly acidic pH-responsive peptide and a nanoparticle containing the peptide. The present invention further relates to a substance delivery agent containing the nanoparticle.

BACKGROUND ART

In cancer chemotherapy, attempts have been made to develop a DDS to improve specificity; however, almost none of these attempts focus on the tumor environment. Specifically, tumor tissues are in a special environment having a pH (a pH around 6.5) lower than that of physiological conditions (a pH around 7.4). However, drug delivery carriers that act in a tumor tissue-specific manner in such a way as to respond to this small pH change have yet to be developed. Until now, to improve the blood-circulating properties while avoiding binding with plasma proteins in the blood, polyethylene glycol (PEG), which is a hydrophilic macromolecule, has been used to modify the surface of liposomes, etc., and the modified liposomes have been used as a carrier of, for example, anticancer drugs (e.g., Patent Literature (PTL) 1). It has, however, been revealed that PEG is antigenic. A carrier displaying PEG on its surface has a low affinity for cells, and is therefore less likely to be taken up by cells; delivering a drug to the inside of tumor cells is thus difficult. The peptide-liposome complex disclosed in PTL 2 retains a positive charge due to the presence of basic amino acid (lysine or arginine) at the N terminal region, and a change in charge does not occur depending on pH; sufficient blood-circulating properties can thus not be expected.

Non-Patent Literature (NPL) 1 uses His segments as a pH-responsive region. According to the technique disclosed in NPL 1, a drastic decrease in the pH of the external environment from 7.4 to 5.0 causes a neutral His to be positively charged, and the thus-increased electrostatic repulsion causes disruption of micelles. However, a His would not be protonated alone at a weakly acidic pH of 6.5; therefore, causing charge reversal at a pH of 6.5 is difficult.

NPL 2 discloses pH-responsive micelles whose surface charge changes from negative to positive when dimethylmaleic acid chemically bonded to a lysine segment at a terminal of a block polymer is dissociated due to a decrease in pH. In the peptide disclosed in NPL 2, dissociation of the dimethylmaleic acid causes exposure of positively charged lysine residues; even if the pH is increased, such a state does not return to the original state. Also in a case where they pass through an inflammation site or other low pH tissues while flowing in the blood circulation, the dimethylmaleic acid would be dissociated to expose lysine, causing interaction with blood components; reaching a target tumor is therefore difficult.

CITATION LIST

Patent Literature

PTL 1: JP2004-10481A

PTL 2: JP2004-523531A

Non-Patent Literature

NPL 1: AIChE Journal Vol. 56, No. 7, 2010, pp. 1922-1931

NPL 2: International Journal of Pharmaceutics 376, 2009, pp. 134-140

SUMMARY OF INVENTION

Technical Problem

An object of the present invention is to provide a drug delivery carrier capable of releasing a target substance in a weakly acidic pH environment such as cancer tissues.

Solution to Problem

The present invention provides the following items (1) to (16), which are directed to a nanoparticle or a substance delivery agent.

(1) A nanoparticle comprising a peptide and a particle-forming component, the particle-forming component forming a liposome or a micelle, and the peptide having a sequence with 2 to 8 units, wherein each of the units starts with His (histidine) and ends with an acidic amino acid, and wherein each of the units is identical or different.

(2) The nanoparticle according to Item (1), wherein each of the units has 2 to 5 amino acids between the His and the acidic amino acid.

(3) The nanoparticle according to Item (1) or (2), wherein each of the units has 3 amino acids between the His and the acidic amino acid.

(4) The nanoparticle according to Item (2) or (3), wherein the amino acids between the His and the acidic amino acid are any amino acids selected from Gly, Ala, His, Leu, Ile, Val, Phe, Tyr, Trp, Cys, Met, Ser, Thr, Gln, and Asn.

(5) The nanoparticle according to Item (4), wherein the amino acids between the His and the acidic amino acid are any amino acids selected from Gly, Ala, His, Cys, and Ser.

(6) The nanoparticle according to any one of Items (1) to (5), wherein the peptide comprises 2 to 8 units represented by Formula (I) below:

$$\text{His-}(AA_1)(AA_2)(AA_3)\text{-Glu/Asp} \quad (I).$$

wherein His is histidine; Glu/Asp is glutamic acid or aspartic acid; and $AA_1$, $AA_2$, and $AA_3$ are the same or different and each represent Gly, Ala, His, Leu, Ile, Val, Phe, Tyr, Trp, Cys, Met, Ser, Thr, Gln, or Asn, and wherein the amino acid sequence of each of the units is the same or different.

(7) The nanoparticle according to Item (6), wherein the peptide has a sequence of any one of SEQ ID Nos: 1 to 3.

(8) The nanoparticle according to any one of Items (1) to (7), wherein the peptide has, at a terminal, a hydrophobic group for being retained by the liposome or miselle.

(9) The nanoparticle according to Item (8), wherein the hydrophobic group is a $C_{12-24}$ hydrocarbon or $C_{12-24}$ acyl group.

(10) The nanoparticle according to any one of Items (1) to (9), wherein the particle-forming component contains phospholipid.

(11) The nanoparticle according to any one of Items (1) to (10), wherein the particle-forming component forms a liposome.

(12) The nanoparticle according to any one of Items (1) to (11), wherein the nanoparticle is loaded with at least one target substance selected from the group consisting of drugs, nucleic acids, peptides, proteins, sugar, and composites thereof.

(13) A substance delivery agent comprising the nanoparticle of any one of Items (1) to (12).

(14) A peptide compound represented by Formula (II) below:

$$R^1—(Z^1)_l[\text{His-}(AA_1)(AA_2)(AA_3)\text{-Glu/Asp}]_n(Z^2)_m—R \quad \text{(II)},$$

wherein His is histidine; Glu/Asp is a glutamic acid or aspartic acid; $AA_1$, $AA_2$, and $AA_3$ are the same or different and each represent Gly, Ala, His, Leu, Ile, Val, Phe, Tyr, Trp, Cys, Met, Ser, Thr, Gln, or Asn; n represents an integer of 2 to 8; l and m are the same or different and each represent 0 or 1; $R^1$ is a $C_{12-24}$ hydrocarbon or a $C_{12-24}$ acyl group; $R^2$ is OH or a C-terminal protecting group; and $Z^1$ or $Z^2$ represents a linker consisting of 1 to 8 amino acids selected from Gly, Ala, Leu, Ile, Val, Phe, Tyr, Trp, Cys, Met, Ser, Thr, Gln, and Asn, the peptide compound containing 10 to 60 amino acids in total.

(15) The peptide compound according to Item (14), wherein the peptide in the peptide compound represented by Formula (II) has a sequence of any one of SEQ ID Nos: 1 to 3.

(16) The peptide compound according to Item (14) or (15), wherein $R^1$ is a $C_{12-24}$ acyl group.

Advantageous Effects of Invention

The present invention can provide a nanoparticle or substance delivery agent capable of releasing an encapsulated target substance in a weakly acidic cellular environment having a pH of about 6.5.

The nanoparticle of the present invention can release a target substance in the above-mentioned weakly acidic region to make the substance act therein, and can thus provide an excellent drug delivery system.

The nanoparticle of the present invention avoids interaction with blood plasma components, etc., under physiological conditions, i.e., pH 7.4, because of the negative electric charge of acidic amino acids, while possessing long blood-circulating properties. In the nanoparticle of the present invention, the presence of an acidic amino acid adjacent to His controls the pH-responsiveness of the His, enabling the nanoparticle of the invention to show sensitive responsiveness even to a weakly acidic pH. For this reason, after reaching a tumor as a result of the EPR effect (Enhanced Permeation and Retention effect), the nanoparticle of the present invention will be protonated under weakly acidic conditions in the tumor environment, causing charge reversal; the nanoparticle of the present invention is thereby taken up by cancer cells. As such, the nanoparticle of the present invention is highly useful.

DESCRIPTION OF EMBODIMENTS

Figure 1:
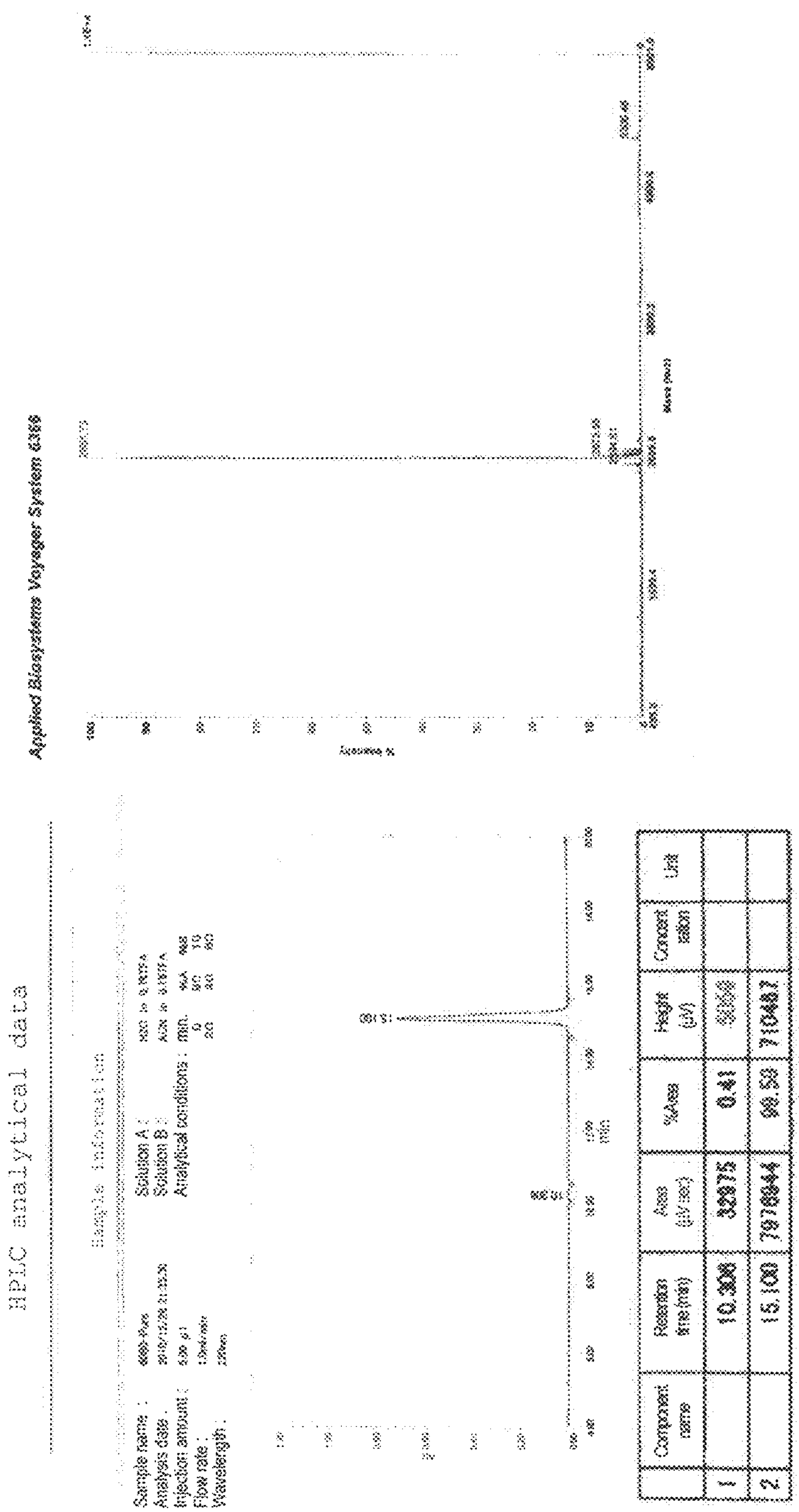
FIG. 1 shows the HPLC and MALDI-TOF-MS results of the stearoylated peptide (SEQ ID NO: 1; C-terminus: $CONH_2$) obtained in Production Example 1.

The nanoparticle of the present invention comprises a particle-forming component and a peptide as constituent elements.

The peptide of the present invention comprises 10 to 60, preferably 12 to 40, and more preferably 14 to 30 amino acids in total.

The peptide of the present invention contains His (histidine, H) and an acidic amino acid (glutamic acid (Glu, E) or aspartic acid (Asp, D) as essential constituent elements, and has a sequence with units each starting with His and ending with an acidic amino acid. Each of these units contains 2 to 5, and preferably 3, amino acids, between His and the acidic amino acid. Each of these units has the same number of amino acids between His and the acidic amino acid. For example, when the initial unit has three amino acids, each subsequent unit also has three amino acids. These amino acids are selected from Gly, Ala, His, Leu, Ile, Val, Phe, Tyr, Trp, Cys, Met, Ser, Thr, Gln, and Asn. Of these, Gly, Ala, His, Cys, and Ser are preferable. The peptide has 2 to 8, preferably 2 to 6, and more preferably 2 to 4, units in total, and the adjacent units are directly bonded to each other. Specifically, His is adjacent to the acidic amino acid at moieties in which the units are bonded to each other.

In one preferable embodiment, the peptide of the present invention has 2 to 8, preferably 2 to 6, and more preferably 2 to 4, units represented by Formula (I) below:

$$\text{His-}(AA_1)(AA_2)(AA_3)\text{-Glu/Asp} \quad \text{(I)}.$$

wherein His is histidine; Glu/Asp is glutamic acid or aspartic acid; and $AA_1$, $AA_2$, and $AA_3$ each represent Gly, Ala, His, Leu, Ile, Val, Phe, Tyr, Trp, Cys, Met, Ser, Thr, Gln, or Asn.

Each of $AA_1$, $AA_2$, and $AA_3$ is preferably Gly, Ala, Ser, Cys, or His, and more preferably Gly, Ala, or His. In the peptide sequence, the total number of His residues is greater than that of acidic amino acids. For example, when 2 acidic amino acids are present, 3 to 7 His residues are present. When 3 acidic amino acids are present, 4 to 10 His residues are present. When 4 acidic amino acids are present, 5 to 13 His residues are present. When 5 acidic amino acids are present, 6 to 16 His residues are present. When 6 acidic amino acids are present, 7 to 19 His residues are present. When 8 acidic amino acids are present, 9 to 25 His residues are present. The peptide of the present invention contains 2 to 8, preferably 2 to 6, more preferably 2 to 4 acidic amino acids. The peptide of the present invention contains 3 to 25, preferably 3 to 19, and more preferably 3 to 13 His residues.

In particular, the unit of the present invention is preferably His-Gly-Ala-His-Glu, His-Ala-Gly-His-Glu, His-Ala-Ala-Gly-Glu, or His-His-Ala-His-Glu. In addition to these units, the peptide of the present invention may have, at the N-terminus or C-terminus, an amino acid sequence ($Z^1$ or $Z^2$; a linker) comprising Gly, Ala, His, and the like. Examples of the amino acids constituting the linker ($Z^1$ or $Z^2$) include Gly, Ala, Leu, Ile, Val, Phe, Tyr, Trp, Cys, Met, Ser, Thr, Gln, and Asn. Of these, Gly, Ala, Ser, and Cys are preferable; and Gly, Ala, and His are more preferable. Each linker ($Z^1$ or $Z^2$) contains 1 to 8, and preferably 2 to 6, amino acids in total.

The peptide of the present invention may have a C-terminal protecting group at the C-terminus. The C-terminal protecting group includes a group that forms an amide with the carbon atom of the C-terminal carboxyl group, or a group that forms an ester with the oxygen atom of the carboxyl group. Examples of the group that forms an ester include alkyl groups, in particular $C_{1-5}$ linear or branched alkyl groups ($C_{1-5}$ alkyl groups), such as methyl, ethyl, and propyl. Examples of the group that forms an amide include amine functional groups, such as amino; and alkyl amino functional groups, such as methylamino, ethylamino, dimethylamino, diethylamino, methylethylamino, and other mono- or di-$C_{1-5}$ alkylamino groups. The group that forms an amide is preferable; amino is more preferable.

The peptide of the present invention is modified with a hydrophobic group. The hydrophobic group is introduced at the N- or C-terminus, preferably N-terminus, of the peptide. The hydrophobic group has 12 or more, preferably 12 to 24, more preferably 14 to 22, and still more preferably 16 to 20, carbon atoms. Examples thereof include hydrocarbon groups and acyl groups. In particular, acyl groups are preferable. The hydrophobic group may have a linear or branched chain. Examples of the hydrocarbon groups include linear or branched alkyl groups having 12 or more carbon atoms, such as dodecyl, tetradecyl, hexadecyl, octadecyl, and eicosyl. Stearyl is preferable. Preferable examples of acyl groups include lauroyl, myristoyl, palmitoyl, stearoyl, behenoyl, isostearoyl, eicosanoyl, lignoceroyl, isopalmitoyl, oleoyl, linoloyl, and the like. Acyl groups selected from lauroyl, myristoyl, palmitoyl, stearoyl, isostearoyl, and oleoyl are more preferable.

Preferable examples of the peptide of the present invention include those having an amino acid sequence of any one of SEQ ID Nos: 1 to 3. In a preferable embodiment, the N-terminus of this peptide is bound to a hydrophobic group for being retained by a liposome or micelle. Another preferable embodiment is a peptide compound represented by Formula (II) below:

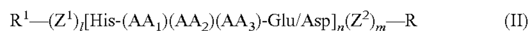

$$R^1—(Z^1)_l[\text{His-}(AA_1)(AA_2)(AA_3)\text{-Glu/Asp}]_n(Z^2)_m—R \qquad \text{(II)}$$

wherein His is histidine; Glu/Asp is a glutamic acid or aspartic acid; $AA_1$, $AA_2$, and $AA_3$ are the same or different and each represent Gly, Ala, His, Leu, Ile, Val, Phe, Tyr, Trp, Cys, Met, Ser, Thr, Gln, or Asn; n is an integer of 2 to 8; l and m are the same or different and represent 0 or 1; $R^1$ is a $C_{12-24}$ hydrocarbon or $C_{12-24}$ acyl group; $R^2$ is OH or a C-terminal protecting group; $Z^1$ or $Z^2$ represents a linker consisting of 1 to 8 amino acids selected from Gly, Ala, Leu, Ile, Val, Phe, Tyr, Trp, Cys, Met, Ser, Thr, Gln, and Asn, the peptide compound containing 10 to 60 amino acids in total. Examples of the hydrocarbon groups, acyl groups, and C-terminal protecting groups are as stated above.

The peptide of the present invention can be produced by a known peptide synthesis method, in particular, a liquid phase synthesis method or a solid phase synthesis method. It is also possible to synthesize the peptide of the present invention by a method comprising introducing DNA encoding a peptide of the present invention into a host cell, and expressing the DNA, using a gene recombination technique. For example, in solid phase synthesis, the peptide of the present invention can be obtained as follows: the carboxyl group of an N-protected amino acid, in which the amino group of the amino acid corresponding to the C-terminus is protected with a urethane protecting group such as 9-fluorenylmethyloxycarbonyl (Fmoc) group, is bonded to an insoluble resin having amino groups; the protecting group of the amino group is then removed to successively condense protected amino acids in the N-terminal direction; and the insoluble resin and the protecting groups of amino acids are removed to thereby obtain the peptide of the present invention. The above-mentioned insoluble resin having amino groups is not particularly limited, but is preferably an Fmoc-NH-SAL resin (4-(2',4'-dimethoxyphenyl-Fmoc-aminoethyl)phenoxy linker resin); a target substance can be directly given thereto by resin cleavage. The protected amino acid used in synthesis of the peptide of the present invention can be obtained by protecting a functional group with a known protecting group by using a known method. It is also possible to use commercially available protected amino acids. As a protecting group, known protecting groups can be used. Examples thereof include methoxycarbonyl, ethoxycarbonyl, tert-butoxycarbonyl, 9-fluorenyl methoxycarbonyl, benzyloxycarbonyl, 4-methoxy benzyloxycarbonyl, 2,2,2-trichloroethyloxycarbonyl, formyl, acetyl, propionyl, butyryl, and the like. To prepare protected amino acids, for example, known methods can be used, such as a DIPCDI-HOBt (diisopropylcarbodiimide-1-hydroxybenzotriazole) method. This condensation reaction can be performed in a known solvent, e.g., an organic solvent such as dimethylformamide. A deprotection reagent for amino-protecting groups is not limited, and a known reagent, such as piperidine/dimethylformamide, can be used to cleave a protecting group such as Fmoc. Deprotection of a urethane protecting group can be performed, for example, by catalytic reduction or with the use of trifluoroacetic acid. Deprotection of other protecting groups can also be performed by a known method. The degree of progress of the condensation reaction in each synthetic step can be confirmed by a known method, such as a ninhydrin reaction method. As such, a protected peptide having a desired amino acid sequence can be obtained. The use of an Fmoc-NH-SAL resin as the insoluble resin can simultaneously remove the resin and protecting group by a treatment with TMSBr (trimethylsilylbromide), TFA (trifluoroacetic acid), or the like. The peptide can be obtained with the C terminus of COOH ($R^2$=0H) or $CONH_2$ ($R^2$=$NH_2$), depending on the type of the resin used.

When $R^2$ is defined as OH, the carboxylic acid of the C-terminal amino acid of the peptide of the present invention is unsubstituted. Likewise, when $R^2$ is defined as $NH_2$, etc., the carboxylic acid of the C-terminal amino acid of the peptide of the present invention is amide ($CONH_2$).

Introduction of a hydrophobic group into the peptide of the present invention can be performed by a known method. For example, a desired acyl group can be introduced through reaction of a peptide with a free N-terminus and a carboxylic acid that corresponds to the acyl group to be introduced, together with a condensation agent (e.g., HBTU/HOBt) and a reaction accelerator (e.g., DIEA). Introduction of a hydrocarbon group can be achieved through reaction with a halogenated hydrocarbon that corresponds to the hydrocarbon group to be introduced, in the presence of a base.

The thus-obtained peptide of the present invention can be isolated and purified by a known means, such as extraction, recrystallization, a variety of chromatography (gel filtration, ion exchange, partition, and adsorption), electrophoresis, and countercurrent distribution. A reversed-phase high-pressure liquid chromatography method is preferable.

The nanoparticle of the present invention has a zeta potential of about −100 to 50 mV, preferably about −50 to 30 mV, more preferably about −30 to 10 mV, and particularly about −30 to 0 mV, at about a neutral pH (e.g., pH 7 or 7.4). Zeta potential can be measured by using a Zetasizer.

The nanoparticles of the present invention have an average particle diameter of, for example, 30 to 1,000 nm, preferably 50 to 500 nm, more preferably 60 to 400 nm, and particularly 70 to 300 nm, although it is not limited thereto. The average particle diameter can be measured, for example, by a dynamic light-scattering method, a static light-scattering method, electron microscope observation, atomic force microscope observation, or the like.

The substance delivery agent of the present invention can be used either in vitro or in vivo to deliver a target substance to a low pH site.

Examples of low pH sites include inflammation sites, tumor sites, infected sites, and the like. In particular, tumor sites are preferable.

Examples of the target substance loaded in the nanoparticle include, but are not particularly limited to, one or more members selected from the group consisting of drugs, nucleic acids, peptides (e.g., oxytocin, bradykinin, thyrotropin-releasing factor, enkephalin, and like biologically active peptides and peptide hormones), proteins (e.g., enzyme, interleukin, and various like cytokines, cell transfer factor, cell growth factor, and antibodies), sugar, and composites thereof. These can be selected according to the purpose, such as diagnosis or treatment. Nucleic acids include DNA and RNA, as well as analogues and derivatives of DNA and RNA (e.g., siRNA, peptide nucleic acid (PNA), and phosphorothioate DNA). Nucleic acids can either be single or double stranded, and can either be linear or circular nucleic acids.

Examples of drugs used as the target substance include anticancer drugs, vasodilator drugs, antimicrobial agents, and the like. Specific examples of anticancer drugs include tegafur, doxorubicin, daunorubicin, cis-platinum, oxaliplatin, carboplatin, paclitaxel, irinotecan, SN-38, actinomycin D, vincristine, vinblastine, methotrexate, azathioprine, fluorouracil, mitomycin C, docetaxel, cyclophosphamide, capecitabine, epirubicin, gemcitabine, mitoxantrone, leucovorin, vinorelbine, trastuzumab, etoposide, estramustine, prednisone, interferon α, interleukin-2, bleomycin, ifosfamide, mesna, altretamine, topotecan, cytarabine, methylprednisolone, dexamethasone, mercaptopurine, thioguanine, fludarabine, gemtuzumab, idarubicin, mitoxantrone, tretinoin, alemtuzumab, chlorambucil, cladribine, imatinib, epirubicin, dacarbazine, procarbazine, mechlorethamine, rituximab, denileukin diftitox, trimethoprim/sulfamethoxazole, allopurinol, carmustine, tamoxifen, filgrastim, temozolomide, melphalan, vinorelbine, azacitidine, thalidomide, mitomycin, and the like. Examples of vasodilator drugs include bosentan, ambrisentan, beraprost sodium, and the like. Examples of antimicrobial agents include amphotericin B, penicillin G, ampicillin, cefazolin, imipenem, aztreonam, gentamicin, tetracycline, chloramphenicol, erythromycin, azithromycin, rokitamycin, telithromycin, quinupristin, phosmidosine, nalidixic acid, norfloxacin, sparfloxacin, linezolid, and the like.

Preferable examples of nucleic acids used as the target substance include any of double stranded RNAs (dsRNAs) selected from the group consisting of meroduplex RNA (mdRNA), nicked dsRNA (ndsRNA), gapped dsRNA (gdsRNA), short interfering nucleic acid (siNA), siRNA, microRNA (miRNA), short hairpin RNA (shRNA), short interfering oligonucleotide, short interfering substituted oligonucleotide, short interfering modified oligonucleotide, chemically modified dsRNA, and post-transcriptional gene silencing RNA (ptgsRNA). The target substance may be used singly or in a combination of two or more. For example, two or more types of siRNAs may be used in combination.

In one embodiment in terms of substitution and modification (including chemical modification), a double stranded RNA may comprise an overhang of one to four nucleotides at one or both 3' ends of the double stranded RNA, such as an overhang comprising a deoxyribonucleotide or two deoxyribonucleotides (e.g., thymidine, adenine). A double stranded RNA may have a blunt end at one or both ends of the double stranded RNA. In one embodiment, the 5' end of the first or second strand is phosphorylated. In any of the embodiments of double stranded RNA, the nucleotide overhangs at the 3' end can comprise ribonucleotides or deoxyribonucleotides that are chemically modified at a nucleic acid sugar, base, or backbone. In any of the embodiments of double stranded RNA, the nucleotide overhangs at the 3' end can comprise one or more universal base ribonucleotides. In any of the embodiments of double stranded RNA, the nucleotide overhangs at the 3' end can comprise one or more acyclic nucleotides. In any of the embodiments of double stranded RNA, dsRNA can further comprise a terminal phosphate group, such as a 5'-phosphate (see Martinez et al., Cell. 110: 563-574, 2002; and Schwarz et al., Molec. Cell. 10: 537-568, 2002) or a 5',3'-diphosphate.

A double stranded RNA can further comprise a 2'-sugar substitution, such as 2'-deoxy, 2'-O-methyl, 2'-O-methoxyethyl, 2'-O-2-methoxyethyl, halogen, 2'-fluoro, 2'-O-allyl, or the like, or a combination thereof. In further embodiments, a double stranded RNA further comprises a terminal cap substituent on one or both ends of the first strand or on one or more of the second strands, such as an alkyl, abasic, deoxy abasic, glyceryl, dinucleotide, acyclic nucleotide, inverted deoxynucleotide moiety, or a combination thereof.

In further embodiments, a double stranded RNA may further comprise at least one modified internucleoside linkage, such as independently a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, boranophosphate linkage, or a combination thereof.

A double stranded RNA can be substituted or modified (including chemical modification) by using 5-methylcytosine; 5-hydroxymethyl cytosine; xanthine; hypoxanthine; 2-aminoadenine; 6-methyl, 2-propyl, or other alkyl derivatives of adenine and guanine; 8-substituted adenines and guanines (e.g., 8-aza, 8-halo, 8-amino, 8-thiol, 8-thioalkyl, 8-hydroxyl); 7-methyl, 7-deaza, and 3-deaza adenines and guanines; 2-thiouracil; 2-thiothymine; 2-thiocytosine; 5-methyl, 5-propynyl, 5-halo (e.g., 5-bromo or 5-fluoro), 5-trifluoromethyl, or other 5-substituted uracils and cytosines; and nucleotide analogues, such as 6-azouracil.

RNAs, such as double stranded RNAs (dsRNAs) may be chemically modified. Examples of such chemical modifications include, but are not limited to, phosphorothioate internucleotide linkages, 2'-deoxyribonucleotides, 2'-O-methyl ribonucleotides, 2'-deoxy-2'-fluoro ribonucleotides, "acyclic" nucleotides, 5'-C-methyl nucleotides, and terminal glyceryl and/or inverted deoxy abasic residue incorporation. These chemical modifications can preserve RNAi activity in cells.

As long as the liposome is a closed vesicle with a lipid bilayer structure, it may be a multilamellar liposome (MLV), or a unilamellar liposome, such as SUV (small unilamellar vesicle), LUV (large unilamellar vesicle), or GUV (giant unilamellar vesicle).

Specific examples of the type of lipid that forms a lipid bilayer in the liposome of the present invention include phosphatidylcholines (e.g., dioleoylphosphatidylcholine, dilauroylphosphatidylcholine, dimyristoylphosphatidylcholine, dipalmitoylphosphatidylcholine, and distearoylphosphatidylcholine), phosphatidylglycerols (e.g., dioleoylphosphatidylglycerol, dilauroylphosphatidylglycerol, dimyristoylphosphatidylglycerol, dipalmitoylphosphatidylglycerol, and distearoylphosphatidylglycerol), phosphatidylethanolamine (e.g., dioleoylphosphatidylethanolamine, dilauroylphosphatidylethanolamine, dimyristoylphosphatidylethanolamine, dipalmitoylphosphatidylethanolamine, distearoylphosphatidylethanolamine), phosphatidylserine, phosphatidylinositol, phosphatidic acid, cardiolipin, and like phospholipids or hydrogen additives thereof; and sphingomyelin, ganglioside, and like glycolipids. These may be used singly or in a combination of two or more. Phospholipids may be synthetic lipids, semi-synthetic lipids, or natural lipids derived from egg yolk, soybean, or other animals or plants (e.g., egg yolk lecithin and soybean lecithin). These lipids may be used singly or in a combination of two or more.

To achieve physical or chemical stabilization of the lipid bilayer, and to adjust the membrane fluidity, the lipid bilayer may comprise one or more members selected from, for example, cholesterol, cholesterol succinic acid, lanosterol, dihydrolanosterol, desmosterol, dihydrocholesterol, and like animal-derived sterols; stigmasterol, sitosterol, campesterol, brassicasterol, and like plant-derived sterols (phytosterols); zymosterol, ergosterol, and like microorganism-derived sterols; glycerol, sucrose, and like saccharides; triolein, trioctanoin, and like glycerine fatty acid esters. The amount thereof is not particularly limited, but is preferably 5 to 40% (molar ratio), and more preferably 10 to 30% (molar ratio), based on the total amount of the lipids constituting the bilayer.

The lipid bilayer may comprise tocopherol, propyl gallate, ascorbyl palmitate, butylated hydroxytoluene, and like antioxidant agents; stearylamine, oleylamine, and like charged materials for providing a positive charge; dicetyl phosphate and like charged materials for providing a negative charge; membrane extrinsic protein, membrane intrinsic protein, and like membrane proteins. The amount thereof can be suitably adjusted.

The nanoparticle of the present invention comprises, on its surface, a peptide containing 10 to 60 amino acids. When the surface of the nanoparticle is modified using the peptide of the present invention, it is preferable that about 1 to 10 mol % of the total lipids constituting the nanoparticle be modified. The liposome surface of a unilamellar liposome is the outer surface of the lipid bilayer, and the liposome surface of a multilamellar liposome is the outer surface of the outermost lipid bilayer. The nanoparticle of the present invention may comprise the aforementioned peptide at a portion other than the surface (e.g., the inner surface of the lipid bilayer).

The nanoparticle of the present invention preferably comprises an auxiliary lipid (helper lipid). Examples of auxiliary lipids include EPC (egg phosphatidylcholine), DLPC (dilinoleoylphosphatidylcholine), DMPC (dimyristoylphosphatidylcholine), DPPC (dipalmitoylphosphatidylcholine), DSPC (distearoylphosphatidylcholine), POPC (palmitoyloleoylphosphatidylcholine), DOPC (dioleoylphosphatidylcholine), DOPE (dioleoylphosphatidylethanolamine), SOPE (stearyloleoylphosphatidylcholine), and the like. Of these, EPC, DOPC, DOPE, and SOPE are preferable.

A production example of liposomes using a hydration method is described below.

Lipids, which are constituent components of a lipid bilayer, and the aforementioned peptide modified with a hydrophobic group or a hydrophobic compound, are dissolved in an organic solvent, followed by removal of the organic solvent by evaporation, thereby obtaining a lipid membrane. Examples of the organic solvent used herein include hydrocarbons, such as pentane, hexane, heptane, and cyclohexane; halogenated hydrocarbons, such as methylene chloride and chloroform; aromatic hydrocarbons, such as benzene and toluene; lower alcohols, such as methanol and ethanol; esters, such as methyl acetate and ethyl acetate; ketones, such as acetone; and the like. These may be used singly or in a combination of two or more. Subsequently, the lipid membrane is hydrated, and stirred or ultrasonicated, thereby producing nanoparticles having the aforementioned peptide on their surface.

Micelles can be prepared by using only the peptide of the present invention containing a hydrophobic group, such as a stearoyl group (preferably acyl). In this case, the peptide also serves as a particle-forming component. Micelles can also be prepared by using the peptide of the present invention in combination with other components, such as phospholipids or surfactants that can form micelles.

As the phospholipid, the phospholipids and auxiliary lipids listed above that form liposomes can be used. As the surfactant (anionic, nonionic, and cationic), the following can be used.

Examples of anionic surfactants include sulfonates, such as alkane sulfonates, paraffin sulfonates, alkylbenzene sulfonates, α-olefin sulfonates, sulfosuccinates, and sulfosuccinate esters (e.g., dioctylsodium and disodium laureth sulfosuccinate), isethionates, acyl isethionates (e.g., sodium 2-lauroyloxyethane sulfonate), and sulfoalkylamides of fatty acids, particularly N-acylmethyltaurides; sulfates, such as alkyl sulfates, ethoxylated alkyl sulfates, sulfated monoglycerides, sulfated alkanolamides, and sulfated fats and oils; carboxylates, such as alkyl carboxylates having a carbon chain length of 12 or more carbon atoms, acyl sarcosinates, sarcosinates (e.g., sodium lauryl sarcosinate), ethoxylated sodium carboxylate salts, carboxylic acids and salts (e.g., potassium oleate and potassium laurate), ether carboxylic acid; ethoxylated carboxylic acids and salts, such as sodium carboxy methyl alkyl ethoxylate; phosphate esters and salts (e.g., lecithin); acyl glutamates (e.g., disodium n-lauroyl glutamate), and mixtures thereof.

Examples of nonionic surfactants include polyoxyethylenes, such as ethoxylated fatty alcohols, ethoxylated alcohols (e.g., octaoxyethylene glycol monohexadecyl ether, C16E8, and C12E8), ethoxylated fatty acids, ethoxylated fatty amines, ethoxylated fatty amides, ethoxylated alkanolamide, and ethoxylated alkylphenols; triesters of phosphoric acid (e.g., sodium dioleyl phosphate); alkyl amido diethylamines; alkyl amido propylbetaines (e.g., cocoamido propylbetaine);

amine oxide derivatives, such as alkyl dimethylamine oxides, alkyl dihydroxyethylamine oxides, alkyl amidodimethylamine oxide, and alkyl amidodihydroxyethylamine oxide; polyhydroxy derivatives, such as polyhydric alcohol esters and ethers (e.g., sucrose monooleate, cetostearyl glucoside, β-octyl glucofuranoside esters, alkyl glucoside having a carbon chain length of 10 of 16 carbon atoms), mono, di, and polyglycerol ethers, and polyglycerol esters (e.g., tetraglycerol monolaurate and monoglyceride, and triglycerol monooleate, (such as TS-T122 produced by Grinsted), diglycerol monooleate (such as TST-T101 produced by Grinsted)), and ethoxylated glycerides; monoglycerides, such as monoolein and monolinolein; and diglyceride fatty acids, such as diglycerol monoisostearate.

Examples of cationic surfactants include aliphatic-aromatic quaternary ammonium halides; quaternary ammonium alkyl amido derivatives; alkylamidopropyldimethylammonium lactate; alkylamidopropyldihydroxyethylammonium lactate; alkylamidopropyl morpholinium lactate; and the like.

The nanoparticle of the present invention in a liposome form can be produced as follows.

Lipids, which are a constituent component of a lipid bilayer, are dissolved in an organic solvent, followed by removal of the organic solvent by evaporation, thereby obtaining a lipid membrane. This lipid membrane is hydrated, and stirred or ultrasonicated to produce nanoparticles. Subsequently, the aforementioned peptide modified with a hydrophobic group or a hydrophobic compound is added to the external liquid of the nanoparticles. The peptide can thereby be introduced onto the surface of each nanoparticle.

In the preparation of nanoparticles, the ratio of cationic lipid (EtOH solution)/auxiliary lipid (EtOH solution)/Chol (EtOH solution) can be suitably changed. When PEG is used for modification, the proportion of PEG is suitably adjusted. For example, PEG may be added in an amount of 0.1 to 15 mol % based on the total amount of lipids.

The nanoparticle of the present invention may encapsulate a target substance that is to be delivered into cells.

When the target substance is water soluble, it is added to an aqueous solvent that is used when a lipid membrane is hydrated during the production of the nanoparticles. The target substance can thereby be encapsulated in the aqueous phase of the nanoparticle. When liposoluble, the target substance is added to the organic solvent used during the production of the nanoparticle; the target substance can thereby be encapsulated in the lipid bilayer of the nanoparticle. The term "encapsulate" as used herein indicates both of the cases where a target substance is included inside a hollow particle such as a nanoparticle, and where a target substance is carried on the surface as a vector, such as a lipid bilayer. Organism species to which a target substance is delivered is not limited as long as it is a vertebrate animal. Mammals are preferable. Examples of mammals include humans, apes, cows, sheep, goats, horse, pigs, rabbits, dogs, cats, rats, mice, guinea pigs, and the like.

The nanoparticle of the present invention may be used in a dispersion state. As a dispersion solvent, a buffer solution such as a physiological saline solution, a phosphate buffer solution, a citrate buffer solution, or an acetic acid buffer solution can be used. To the dispersion, additives may be added, such as a saccharide, a polyhydric alcohol, a water soluble polymer, a non-ionic surfactant, an antioxidant agent, a pH regulator, and a hydration accelerator.

The nanoparticle of the present invention may also be used in a dried dispersion state (e.g., freeze-dried or spray-dried). The dried nanoparticles may be added to a buffer solution, such as a physiological saline solution, a phosphate buffer solution, a citrate buffer solution, or an acetic acid buffer solution, to prepare a dispersion.

The nanoparticles may be used both in vitro and in vivo. When the nanoparticles are used in vivo, the administration route may be, for example, intravenous injection, intravenous drip, or the like. The dosage and administration frequency can be suitably adjusted according to the type and amount of the target substance encapsulated in each of the nanoparticles of the present invention.

The nanoparticle of the present invention causes neither body weight loss nor hepatopathy, and can therefore be administered safely.

EXAMPLES

The present invention is described below in more detail with reference to Production Examples and Examples. However, the scope of the present invention is not limited to these Examples.

Production Example 1

Synthesis of Stearoylated Peptide (Compound 1)

Compound 1: $C_{17}H_{35}$—C(O)-GGGGHGAHEHAGHEHAAGEHHAHE-$NH_2$

Using a Rink amide resin (0.67 mMol/g) as a starting material, with a scale of 0.1 mM or 0.03 mM, the peptide of SEQ ID NO: 1 (C-terminus: $CONH_2$) was synthesized by Fmoc solid-phase synthesis using amino acids, a condensation agent (HBTU/HOBt), and a reaction accelerator (DIEA) (4 equivalents each relative to the resin). A stearic acid (M.W. 284.48), a condensation agent (HBTU/HOBt), and a reaction accelerator (DIEA) (4 equivalents each relative to the resin) were added to the resin to cause activation, and the resulting product was then added to the resin in a state in which extension of amino acids had been completed, leaving only the N terminus free, and reacted overnight at room temperature. (HBTU: M.W. 379.2; HOBt: Anhydrous, M.W. 135.1, DIEA: M.W. 129.2). After completion of the reaction, a TFA (trifluoroacetic acid) cocktail solution (TFA: 125 mL; $H_2O$: 0.25 mL; phenol: 0.375 g; ethanedithiol: 0.125 mL; and thioanisole: 0.25 mL) was added to the resin and reacted under ice cooling for 15 minutes, and at room temperature for 2 hours, to obtain crude peptide. Purification was performed by HPLC, followed by lyophilization. Purity was measured by HPLC and MALDI-TOF-MS. Analysis was performed under the following HPLC conditions, and the target product was obtained as a single peak (retention time 15.1 min).

A Buffer: 0.1% TFA/$H_2O$; B Buffer: 0.1% TFA/acetonitrile; Column: SunFire C18 Column, 5 μm, 4.6×150 mm; Flow rate: 1 mL/min;

Wavelength: 220 nm.

An Applied Biosystems Voyager System was used for MALDI-TOF-MS.

Molecular weight calcd.: 2651.8. found: 2651.73. FIG. 1 shows the results of HPLC and MALDI-TOF-MS.

Synthesis scale: a 0.1-mM scale (molecular weight: 2651.8); Amount of resin used: 159.8 mg; Theoretical value of the peptide obtained by using this resin: 283.9 mg; Crude amount actually obtained: 183.1 mg (yield: 64.5%).

Production Example 2

Synthesis of 4AA-Reduced Peptide (Compound 2)

Compound 2: $C_{17}H_{35}$—C(O)-GGGGHGAHEHAGHE-HAAGEH-$NH_2$

Synthesis was performed as in Production Example 1 to obtain a target peptide. The target peptide contained a stearoyl group (stearic acid amide) at the N-terminus, and $CONH_2$ at the C-terminus. The peptide had an amino acid sequence of SEQ ID NO: 2.

Figure 2:
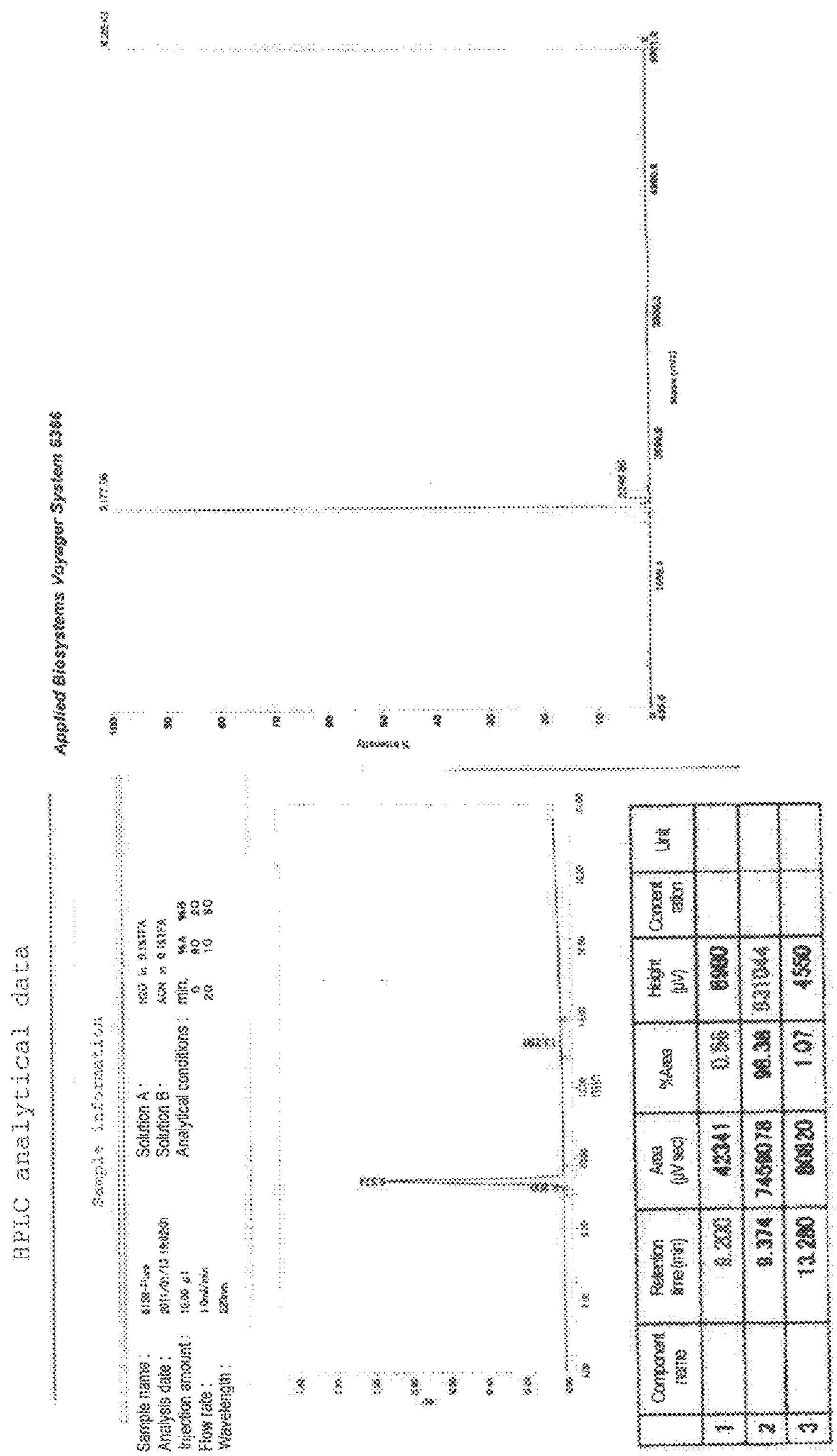
FIG. 2 shows the HPLC and MALDI-TOF-MS results of the stearoylated peptide (SEQ ID NO: 2; C-terminus: $CONH_2$) obtained in Production Example 2.

Molecular weight calcd. of the target stearoylated peptide: 2177.3. found: 2177.9. FIG. 2 shows the results of HPLC and MALDI-TOF-MS.

Synthesis scale: a 0.03-mM scale (molecular weight: 2177.3);

Amount of resin used: 61.2 mg; Theoretical value of the peptide obtained by using this resin: 89.3 mg; Crude amount actually obtained: 28.3 mg (31.7% of yield).

Production Example 3

Synthesis of 8AA-Reduced Peptide (Compound 3)

Compound 3: $C_{17}H_{35}$—C(O)-GGGGHGAHEHAGHEHA-$NH_2$

Synthesis was performed as in Production Example 1 to obtain a target peptide. The target peptide contained a stearoyl group (stearic acid amide) at the N-terminus, and $CONH_2$ at the C-terminus. The peptide had an amino acid sequence of SEQ ID NO: 3.

Figure 3:
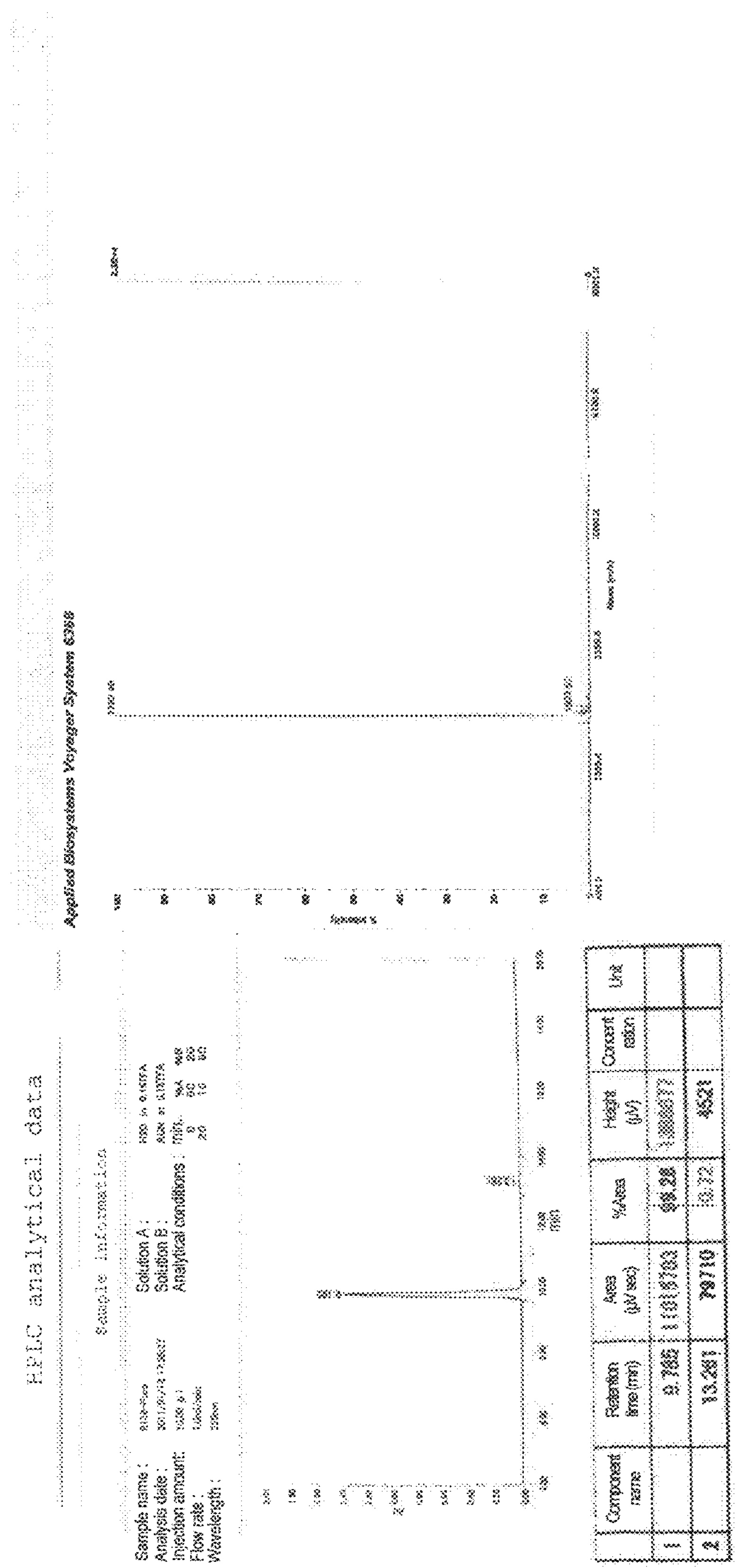
FIG. 3 shows the HPLC and MALDI-TOF-MS results of the stearoylated peptide (SEQ ID NO: 3; C-terminus: $CONH_2$) obtained in Production Example 3.

Molecular weight calcd. of the target stearoylated peptide: 1782.9. found: 1782.4. FIG. 3 shows the results of HPLC and MALDI-TOF-MS.

Synthesis scale: a 0.03-mM scale (molecular weight: 1782.9);

Amount of resin used: 67.0 mg; Theoretical value of the peptide obtained by using this resin: 80.0 mg; Crude amount actually obtained: 51.4 mg (yield: 64.3%).

Production Example 4

Synthesis of Scrambled Peptide (Comparative Compound)

Compound 4: $C_{17}H_{35}$—C(O)-GGGGHGEAHHAEGH-HAEAHHGEAH-$NH_2$

Synthesis was performed as in Production Example 1 to obtain a target peptide. The target peptide contained a stearoyl group (stearic acid amide) at the N-terminus, and $CONH_2$ at the C-terminus. The peptide had an amino acid sequence of SEQ ID NO: 4.

Figure 4:
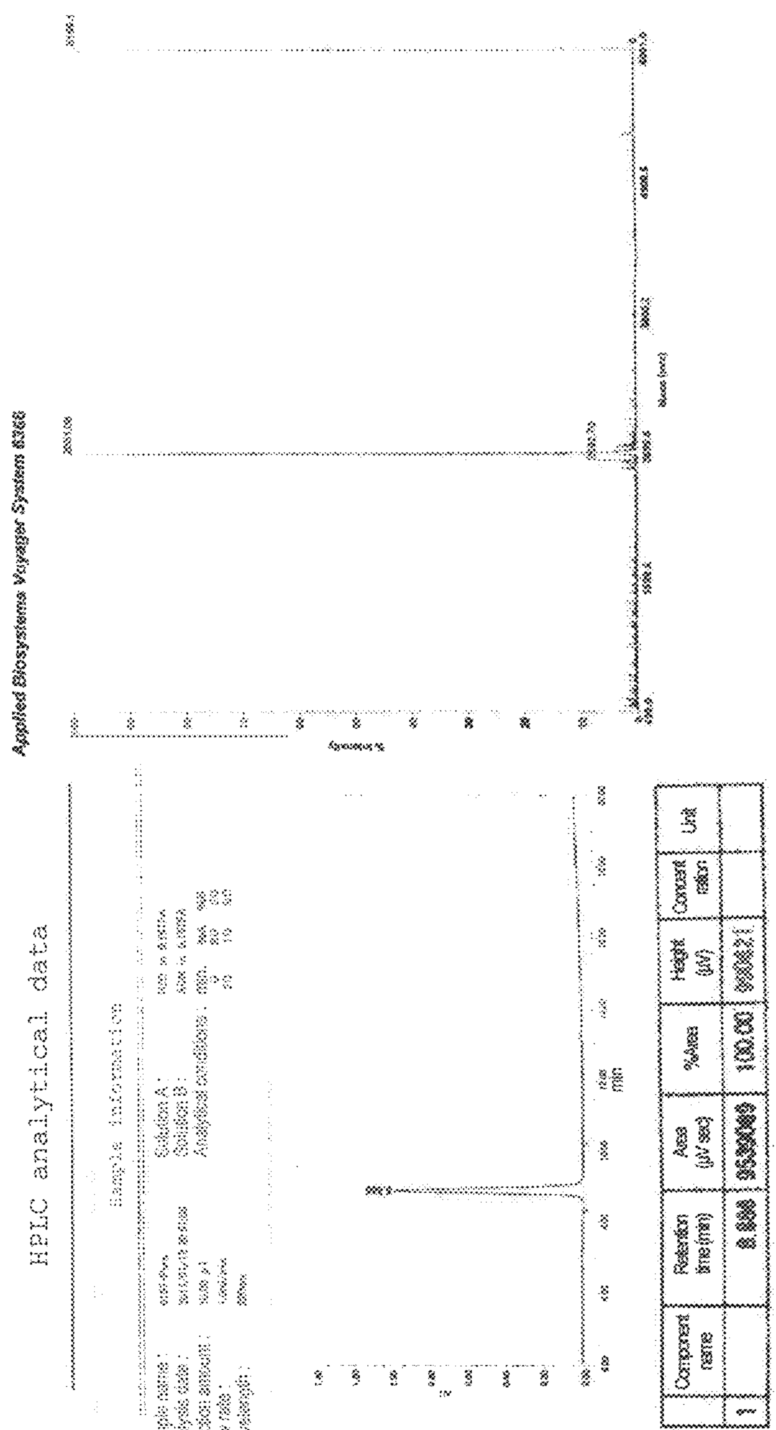
FIG. 4 shows the HPLC and MALDI-TOF-MS results of the stearoylated peptide (SEQ ID NO: 4; C-terminus: $CONH_2$) obtained in Production Example 4.

Molecular weight calcd. of the target stearoylated peptide: 2651.8. found: 2651.0. FIG. 4 shows the results of HPLC and MALDI-TOF-MS.

Synthesis scale: a 0.03-mM scale (molecular weight: 2651.8);

Amount of resin used: 45.3 mg; Theoretical value of the peptide obtained by using this resin: 80.5 mg; Crude amount actually obtained: 31.0 mg (yield: 38.5%).

Example 1

Measurement Results of Particle Diameter and Surface Potential (Zeta Potential) Under Different pH Conditions (Presenting pH-Responsiveness)

(1) Liposomes were prepared as follows. Specifically, a lipid ethanol solution prepared from a mixture of egg yolk phosphatidylcholine (EPC) and dioleoyl tetraammonium propane (DOTAP) at a ratio of 8:1 (mol ratio) was dispensed into test tubes, and an equal amount of chloroform was mixed therewith, followed by evaporation to dryness under a stream of nitrogen to obtain thin lipid membranes. A buffer solution having a pH of 7.4 was added thereto, and the mixture was sufficiently hydrated at room temperature for 10 minutes. After completion of hydration, the test tubes were ultrasonicated using a water tank-type ultrasonic device to prepare liposomes (lipid concentration: 10 mM). To the obtained liposomal suspension was added the peptide (compound 1) obtained in Production Example 1 in an amount of 5 mol % of the total lipid content, and the mixture was incubated. The electrostatic interaction caused binding of the peptide to the lipid membrane surface, and the stearyl group of the peptide was moved to (stuck in) the hydrophobic moiety of membrane lipids. Liposome 1, whose surface was modified with the peptide, was thereby prepared.

(2) The particle diameter (size) and surface potential (ζ potential) of liposome 1 diluted and suspended in buffer solutions having different pH were measured by a Zetasizer Nano produced by Malvern Instruments Ltd. Table 1 shows the results.

TABLE 1

| | pH | | | |
|---|---|---|---|---|
| | 7.4 | 6.5 | 6.0 | 5.5 |
| Size (nm) | 173 ± 7.59 | 265 ± 43.38 | 198 ± 14.5 | 158 ± 5.4 |
| ζ potential (mV) | −15.3 ± 1.32 | 7.13 ± 0.75 | 10.73 ± 1.89 | 11.2 ± 1.24 |

When the pH was 7.4, the particle diameter was slightly less than 200 nm. Even when the pH value was decreased, no great change was observed in the particle diameter. The surface potential was about −15 mV when the pH was 7.4; however, the surface potential was increased to 7 mV when the pH was 6.5. This indicates that the surface electric charge changes from negative to positive due to a slight variation in pH.

Example 2

Figure 5:
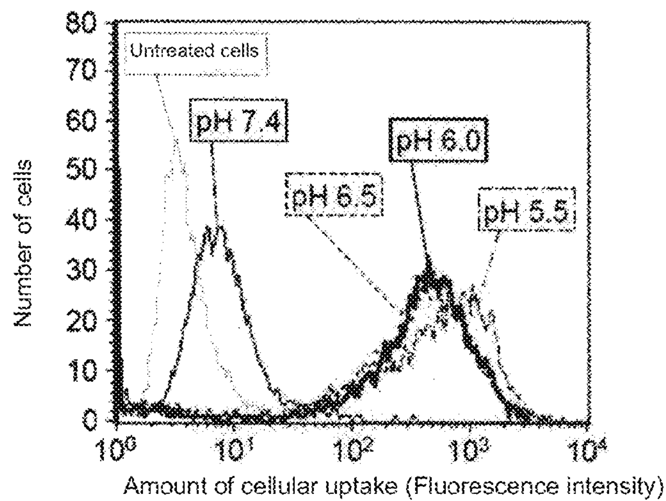
FIG. 5 shows the results obtained by measuring the amount of fluorescent dye in cells using a flow cytometer.

Measurement Results of Cellular Uptake Under Different pH Conditions (Presenting pH-Responsiveness) Liposomes were Prepared as in the Preparation Method of Example 1, except that fluorescent dye-labeled lipids (rhodamine-labeled dioleoylphosphatidylethanolamine) were added in advance to the lipid solution in an amount of 1 mol % of the lipid content. The relevant prepared liposomes were added to cultured mouse melanoma cells (B16-F1) in culture media having different pH (5.5, 6.0, 6.5, and 7.4), and incubated at 37° C. for 1 hour. Thereafter, the culture supernatants were removed therefrom, and the cells were harvested by trypsinization. The amount of the fluorescent dye in the cells (the amount of cellular uptake of liposomes) was measured by a flow cytometer (FACS caliber flow cytometer). FIG. 5 shows the results.

When the pH was 7.4, the amount of cellular uptake of the relevant liposomes was almost the same as that of untreated cells (liposomes not added). In contrast, when the pH was 5.5 or 6.5, a large number of relevant liposomes were taken up by the cells. Specifically, the amount of cellular uptake of the relevant liposomes was remarkably increased by slightly changing the pH value (from 7.4 to 6.5).

Figure 6:
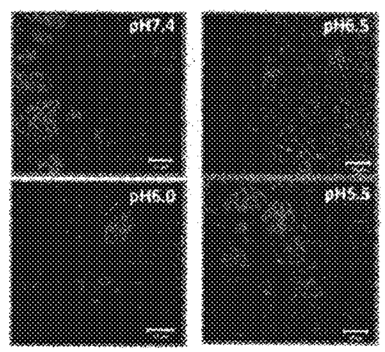
FIG. 6 shows the results obtained by observing cells using a confocal laser scanning microscope (Zeiss LSM 510 META).

The cells here were observed using a confocal laser scanning microscope (Zeiss LSM 510 META). FIG. 6 shows the results. When the pH was 7.4, almost no fluorescence (red) of the relevant liposomes was observed in the cells. In contrast, when the pH was 6.5 or 5.5, a large amount of fluorescence of the relevant liposomes was observed in the cytoplasm (the blue is the nucleus stained with Hoechst 33342). This also indicates that the amount of cellular uptake of the relevant liposomes was significantly increased by slightly changing the pH (from 7.4 to 6.5).

Example 3

Observation Results of Intracellular Dynamics in Cultured Cell System (Presenting pH-Responsiveness in Endosome)

Figure 7:
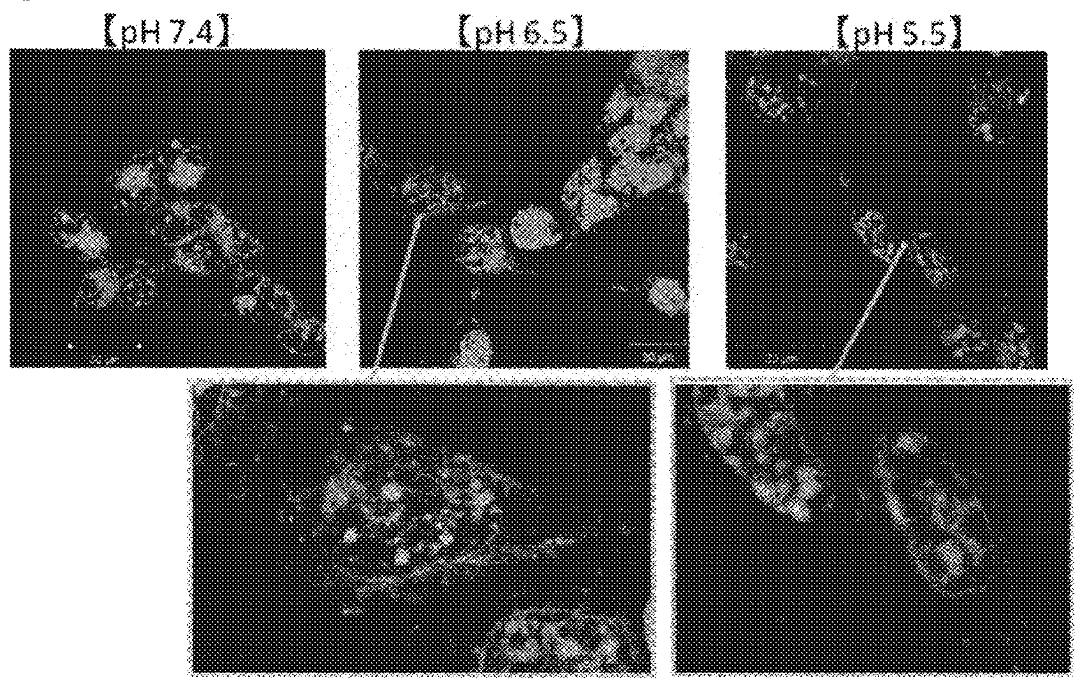
FIG. 7 shows the results obtained by observing a nucleus stained with Hoechst33342 (blue) and endosome/lysosome stained with LysoTracker Green (green) using a confocal laser scanning microscope (Zeiss LSM 510 META).
Figure 8:
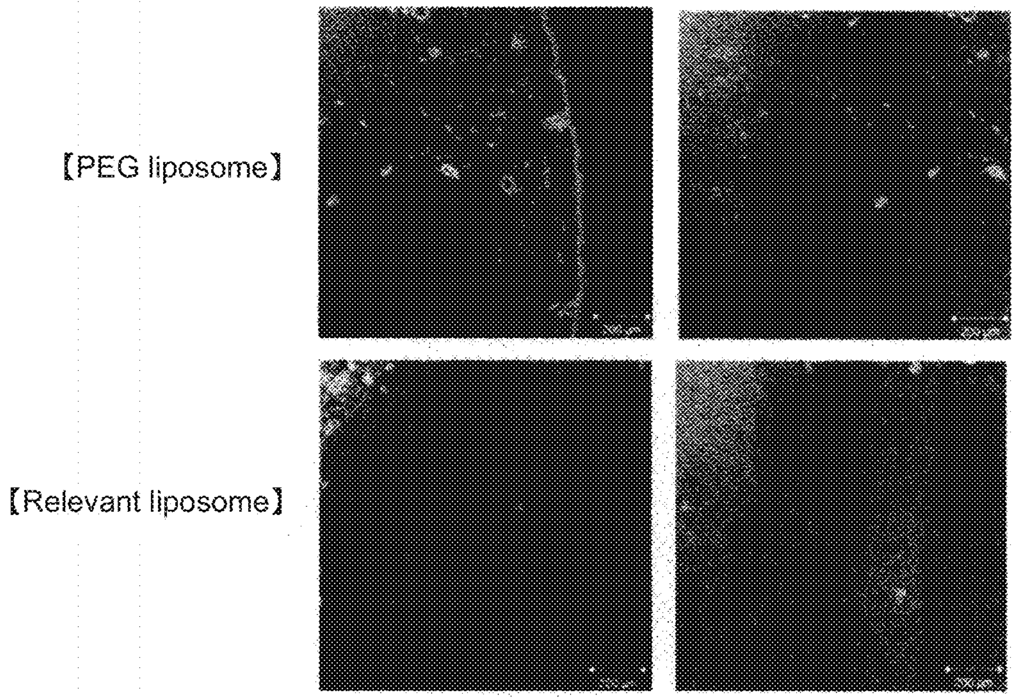
FIG. 8 shows the evaluation results of intratumoral dynamics of cancer-bearing mice of Example 4.

As in Example 2, the fluorescent-labeled relevant liposomes (red) were added to cultured mouse melanoma cells (B16-F1) in culture media having different pH (5.5, 6.0, 6.5, and 7.4), and incubated at 37° C. for 1 hour. Thereafter, the nucleus was stained with Hoechst 33342 (blue), while the endosome and lysosome were stained with LysoTracker green (green). Observation was then performed using a confocal laser scanning microscope (Zeiss LSM 510 META). FIG. 7 shows the results.

The results were similar to those of Example 2; specifically, when the pH was 7.4, almost no red stains were observed within the cells, indicating that the relevant liposomes were not taken up by the cells. In contrast, when the pH was 6.5 or 5.5, a large number of red stains were observed within the cells, indicating that many relevant liposomes were taken up by the cells. The red stains were not overlapped with green stains; almost all the stains were only red. This means that the relevant liposomes did not remain in the endosome or lysosome, and escaped into the cytoplasm. Endosomes and lysosomes have a low pH environment thereinside. Considering this, the possibility is suggested that the relevant liposomes were altered to, for example, fuse with endosomal or lysosomal membranes to thereby escape from endosomes or lysosomes. This confirms that the relevant liposomes have the ability to escape from endosomes and lysosoms in response to pH changes in endosomes and lysosomes.

Example 4

Dynamics in Tumor of Cancer-Bearing Mouse (Presenting pH-Responsiveness in Tumor)

0.2 mL of the relevant liposomes containing a fluorescent dye (CellTracker CM-DiI (red)) at a concentration of 0.5% of the lipid content (lipid concentration: 10 mM), or, as a control, 0.2 mL of polyethylene glycol (PEG)-modified liposomes containing, similar to the above, CellTracker CM-DiI at a concentration of 0.5% of the lipid content (lipid composition:EPC:cholesterol:PEG2000-modified distearoylphosphatidylethanolamine=1.85:1:0.15; lipid concentration: 10 mM) was intravenously injected via tail vein into a cancer-bearing hairless mouse with a tumor grown to a size of 100 $mm^3$, formed by subcutaneous transplantation of B16-F1 cells. Thereafter, the tumor was excised and cryosectioned. The cryosections were treated with 4% paraformaldehyde to fix the tissue, followed by treatment using the anti-CD31 antibody (antibody against endothelial cell marker protein) as a primary antibody. Subsequently, additional treatment was performed using a fluorescent dye (Alexa488 (green))-labeled antibody as a secondary antibody to immunostain the fixed tissue. Further, the same fixed tissue was embedded in Vectashield containing a nuclear dye (DAPI). The thus-obtained embedded and fixed tissue was observed with a confocal laser scanning microscope. Table 8 shows the results.

Both of the liposomes (red) were equally observed in the tumor tissue. This suggests that the relevant liposomes had substantially the same long blood-circulating properties as PEG, although the relevant liposomes were not coated with PEG. Further, many of the PEG liposomes (red) were observed together with green (yellow); this suggests that the PEG liposomes were located within blood vessels and around blood vessels. It is thereby assumed that PEG liposomes are likely to be leaked from tumor tissues. In contrast, regarding the relevant liposomes, red was observed alone away from green, which suggests that the relevant liposomes were located away from the blood vessels, i.e., deep in the tumor tissue. This indicates that the relevant liposomes are likely to remain in tumors (have an excellent targeting effect).

Example 5

CD Spectra of a Peptide Alone or a Peptide-Modified Nanoparticle Under Different pH Conditions (Presenting pH-Responsiveness and the Necessity of a Membrane Structure Substrate)

Figure 9:
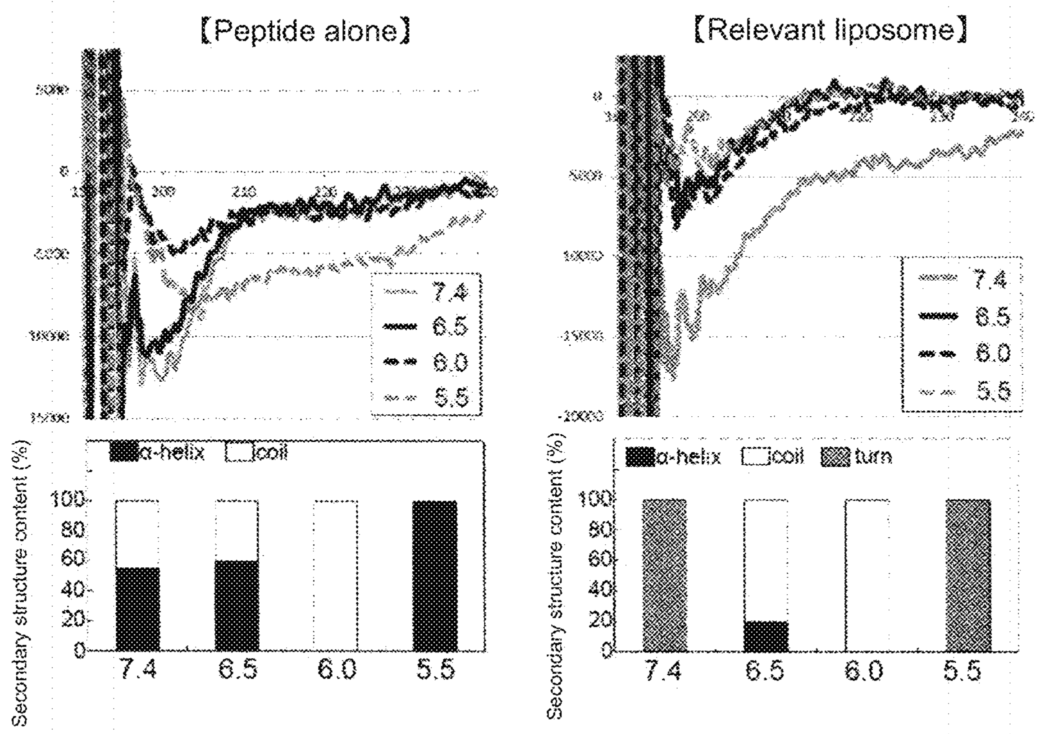
FIG. 9 shows the CD spectra of the peptide alone and the peptide-modified nanoparticles, as well as the predicted results of the composition of the secondary structure.

The peptide obtained in Production Example 1 alone and liposome 1 obtained as in Example 1 (each having a peptide concentration of 20 μM) were suspended in PBS (−) having different pH, and CD (circular dichroism) spectra were recorded on a J-720WI spectropolarimeter (produced by JASCO Corporation). Then, analysis software (see JWSSE-480; Molecular Membrane Biology, July, August 2007; 24 (4): 282-293) was used to predict the composition of the secondary structure in the spectra. FIG. 9 shows the results.

In FIG. 9 below, the "α-helix" represents an a helix structure; the "coil" represents a random coil structure (not forming a clear secondary structure); and "turn" represents a bending structure.

According to the results obtained with the use of the peptide alone, CD spectra obtained when the pH values were 7.4 and 6.5 were almost the same, and the spectrum was greatly changed when the pH was 6.0. This confirms that a structural change does not occur unless the pH is lowered to 6.0 when the peptide is used alone.

In view of the CD spectra of liposome 1, the spectrum of liposome 1 when the pH was 7.4 was different from that obtained with the use of the peptide alone. It is thereby suggested that because of the peptide being located on the lipid membrane, the state of the secondary structure was different from that when the peptide was used alone. Further, the change in pH from 7.4 to 6.5 resulted in a great change in the CD spectrum, the result of which was almost the same as the results obtained when the pH values were 6.0 and 5.5. This clarifies the fact that the peptide located on liposome 1 undergoes a big structural change due to a small pH change. It is thereby confirmed that a particle or membrane structure such as a liposome or a micelle is essential for ensuring the sensitivity of the peptide to a small pH change.

Example 6

Evaluation Results of pH-Responsiveness (Particle Diameter, Zeta Potential, Cell Uptake, Etc.) Regarding a Peptide Having a Shuffled Sequence and Regarding a Peptide of a Different Length (1) As in the preparation method of Example 1, the stearoylated peptides of Production Examples 2 to 4 were added to respective liposomal suspensions each containing EPC and DOTAP at a ratio of 8:1 (molar ratio), and the mixtures were incubated to thereby prepare peptide-modified liposomes 2 to 4, the surface of each being modified with the respective peptides.

(2) The particle diameter (size) and surface potential potential) of each of the peptide-modified liposomes diluted and suspended in buffer solutions having different pH were measured by a Zetasizer Nano produced by Malvern Instruments Ltd.

Table 2 shows the results of peptide-modified liposome 4 obtained by using the peptide of Production Example 4.

TABLE 2

| | pH | | | |
|---|---|---|---|---|
| | 7.4 | 6.5 | 6.0 | 5.5 |
| Size (nm) | 1471 ± 717.6 | 723.3 ± 522.8 | 683.5 ± 46.8 | 945.6 ± 549.8 |
| ζ potential (mV) | 8.2 ± 2.1 | 11.3 ± 3.0 | 12.3 ± 1.5 | 11.1 ± 3.6 |

Liposome 4 having no repeats of the unit starting with His and ending with an acidic amino acid had a positive surface potential at all pHs. Liposome 4 was therefore completely different from the liposomes of the present invention in terms of their properties.

Figure 10:
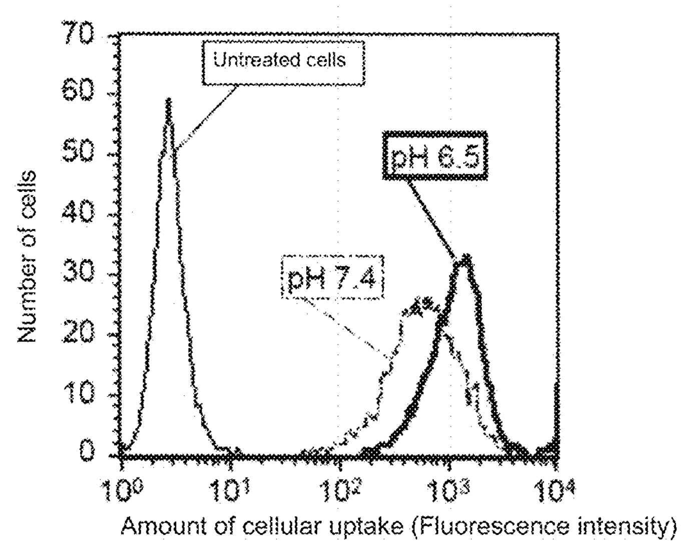
FIG. 10 shows the results of the cellular uptake of the scrambled sequence peptide-modified liposome obtained in Production Example 4, evaluated using an FACS.
Figure 11:
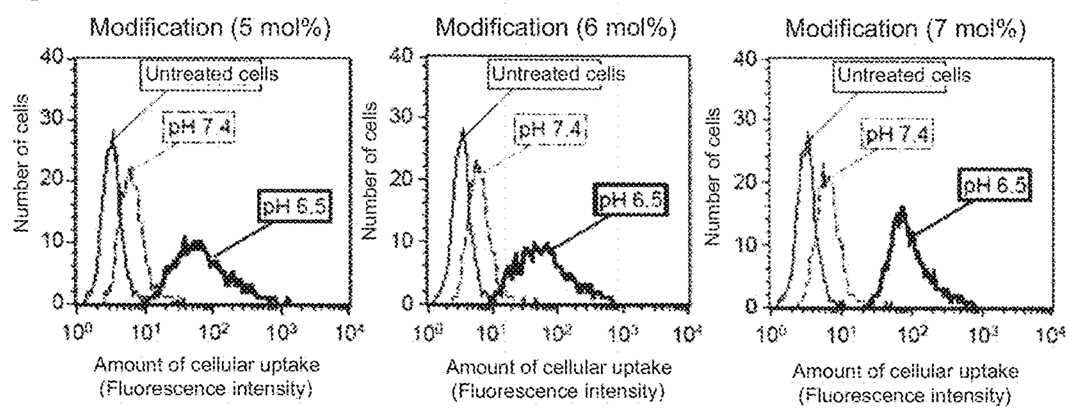
FIG. 11 shows the results of the cellular uptake of the peptide-modified liposome obtained in Production Example 2, evaluated using an FACS.

The cellular uptake of liposome 4 was evaluated by FACS. When the pH was 7.4, a large amount of liposome 4 was taken up by the cells; even when the pH was lowered to 6.5, almost the same amount was taken up by the cells (FIG. 10). These results conform to the results obtained in relation to the surface potential shown above, indicating that even with the same constituent amino acids, liposome 4 having no repeats of the unit starting with His and ending with an acidic amino acid is not responsive to small pH changes.

(3) As in the method of Example 1, liposomes 2a, 2b, and 2c were prepared by using the peptide of Production Example 2, which has 4 residues shorter than the peptide obtained in Production Example 1, in respective amounts of 5, 6, and 7 mol % of the lipid content for modification, and the surface potential was measured. As a result, all the liposomes showed a tendency similar to that of liposome 1 (Table 3).

TABLE 3

| | pH | | | |
|---|---|---|---|---|
| | 7.4 | 6.5 | 6.0 | 5.5 |
| **Peptide (4 residues shortened)-modified liposome (peptide modification: 5 mol % of lipid content)** | | | | |
| Size (nm) | 172.9 ± 717.6 | 152.4 ± 23.1 | 185.1 ± 41.3 | 438.6 ± 538.0 |
| ζ potential (mV) | −14.1 ± 2.3 | −2.3 ± 4.4 | 0 ± 1.5 | 6.6 ± 0.8 |
| **Peptide (4 residues shortened)-modified liposome (peptide modification: 6 mol % of lipid content)** | | | | |
| Size (nm) | 170.9 | 195.6 | | |
| ζ potential (mV) | −12.4 | −3.3 | | |
| **Peptide (4 residues shortened)-modified liposome (peptide modification: 7 mol % of lipid content)** | | | | |
| Size (nm) | 194.4 | 212.5 | | |
| ζ potential (mV) | −12.0 | −2.8 | | |

Further, the cellular uptake was evaluated by FACS. As a result, when the pH was 7.4, the amounts of cellular uptake of all of these liposomes were almost the same as that of a case where untreated cells were involved, i.e., almost no liposomes were taken up by the cells; however, the amounts of cellular uptake increased when the pH was 6.5.

This confirms that even when liposomes were modified with 4 residue-shortened peptide, they would respond to small pH changes, thereby significantly increasing their affinity for cells.

(4) Further, as in the method of Example 1, liposomes 3a, 3b, and 3c were prepared by using the peptide of Production Example 3, which has 8 residues shorter than that of Production Example 1, in respective amounts of 5, 7.5, and 10 mol % of the lipid content for modification, and the surface potential of each liposome was measured (Table 4).

TABLE 4

| | pH | | | |
|---|---|---|---|---|
| | 7.4 | 6.5 | 6.0 | 5.5 |
| **Peptide (8 residues shortened)-modified liposome (peptide modification: 5 mol % of lipid content)** | | | | |
| Size (nm) | 1572 | 561.9 | 225.4 | 175 |
| ζ potential (mV) | 0.5 | 7.8 | 9.0 | 9.8 |
| **Peptide (8 residues shortened)-modified liposome (peptide modification: 7.5 mol % of lipid content)** | | | | |
| Size (nm) | 574.3 | 392.9 | 325.4 | 424.4 |
| ζ potential (mV) | −4.6 | 3.78 | 7.8 | 10.5 |
| **Peptide (8 residues shortened)-modified liposome (peptide modification: 10 mol % of lipid content)** | | | | |
| Size (nm) | 526.5 | 386.9 | 498.2 | 252.9 |
| ζ potential (mV) | −4.8 | 7.1 | 6.7 | 11.1 |

As a result, all of these liposomes showed a big difference in the surface potential between the pH values of 7.4 and 6.5. In particular, liposome 3c, in which 10 mol % of the lipid content was modified, had a large surface potential.

The invention claimed is:

1. A peptide compound represented by Formula (II) below:

$$R^1—(Z^1)_l\text{-}[\text{His-}(AA_1)(AA_2)(AA_3)\text{-Glu/Asp}]_n\text{-}(Z^2)_m—R^2 \quad \text{(II)},$$

wherein His is histidine; Glu/Asp is a glutamic acid or aspartic acid; $AA_1$, $AA_2$, and $AA_3$ are the same or different and each represent Gly, Ala, His, Leu, Ile, Val, Phe, Tyr, Trp, Cys, Met, Ser, Thr, Gln, or Asn; n represents an integer of 2 to 8; l and m are the same or different and each represent 0 or 1; $R^1$ is a $C_{12-24}$ hydrocarbon or a $C_{12-24}$ acyl group; $R^2$ is OH or a C-terminal protecting group; and $Z^1$ and $Z^2$ each represent a linker consisting of 1 to 8 amino acids selected from Gly, Ala, Leu, Ile, Val, Phe, Tyr, Trp, Cys, Met, Ser, Thr, Gln, and Asn, the peptide compound containing 10 to 60 amino acids in total.

2. The peptide compound according to claim 1, wherein the peptide in the peptide compound represented by Formula (II) has a sequence of any one of SEQ ID Nos: 1 to 3.

3. The peptide compound according to claim 1, wherein $R^1$ is a $C_{12-24}$ acyl group.

* * * * *

SEQUENCE LISTING

```
<160> NUMBER OF SEQ ID NOS: 4

<210> SEQ ID NO 1
<211> LENGTH: 24
<212> TYPE: PRT
<213> ORGANISM: Artificial
```

-continued

<220> FEATURE:
<223> OTHER INFORMATION: Synthetic peptide

<400> SEQUENCE: 1

Gly Gly Gly Gly His Gly Ala His Glu His Ala Gly His Glu His Ala
1 5 10 15

Ala Gly Glu His His Ala His Glu
20

<210> SEQ ID NO 2
<211> LENGTH: 20
<212> TYPE: PRT
<213> ORGANISM: Artificial
<220> FEATURE:
<223> OTHER INFORMATION: Synthetic peptide

<400> SEQUENCE: 2

Gly Gly Gly Gly His Gly Ala His Glu His Ala Gly His Glu His Ala
1 5 10 15

Ala Gly Glu His
20

<210> SEQ ID NO 3
<211> LENGTH: 16
<212> TYPE: PRT
<213> ORGANISM: Artificial
<220> FEATURE:
<223> OTHER INFORMATION: Synthetic peptide

<400> SEQUENCE: 3

Gly Gly Gly Gly His Gly Ala His Glu His Ala Gly His Glu His Ala
1 5 10 15

<210> SEQ ID NO 4
<211> LENGTH: 24
<212> TYPE: PRT
<213> ORGANISM: Artificial
<220> FEATURE:
<223> OTHER INFORMATION: Synthetic peptide

<400> SEQUENCE: 4

Gly Gly Gly Gly His Gly Glu Ala His His Ala Glu Gly His His Ala
1 5 10 15

Glu Ala His His Gly Glu Ala His
20